United States Patent [19]

Ui et al.

[11] 4,132,768

[45] Jan. 2, 1979

[54] ULTRAMICRO-QUANTITATIVE DETERMINATION OF ACETONE AND KIT SUITABLE THEREFOR

[75] Inventors: Michio Ui; Yukiko Tokumitsu, both of Sapporo, Japan

[73] Assignee: Michio Ui, Hokkaido, Japan

[21] Appl. No.: 818,344

[22] Filed: Jul. 22, 1977

[30] Foreign Application Priority Data

Aug. 27, 1976 [JP] Japan ............................. 51-101632

[51] Int. Cl.$^2$ ........................................... G01N 33/16
[52] U.S. Cl. ..................................... 424/1; 206/569; 23/230 B
[58] Field of Search .................... 206/569; 424/1, 1.5; 23/230 B

[56] References Cited

PUBLICATIONS

Peden, J. of Lab Clin. Med., vol. 63, No. 2, Feb., 1964, pp. 332–343.
Siegel et al., Clin. Chem., vol. 23, No. 1, Jan, 1977, pp. 46–49.

*Primary Examiner*—Benjamin R. Padgett
*Assistant Examiner*—Christine M. Nucker
*Attorney, Agent, or Firm*—Wenderoth, Lind & Ponack

[57] ABSTRACT

Process for ultramicro-quantitative determination of acetone comprising (1) reacting radioactive molecular or cationic iodine with the acetone contained in a sample from biological preparations in a strong alkaline solution to produce radioactive iodoform according to a haloform reaction quantitatively, (2) reducing the non-reacted molecular or cationic radioactive iodine to a radioactive iodide, (3) separating the radioactive iodoform from the radioactive iodide, and (4) measuring the radioactivity of the radioactive iodoform by any conventional method. Two types of assay kits suitable for use in this determination of acetone comprise respectively:

(A)

Reagent 1 = a radioactive iodide;
Reagent 2 = an oxidizing agent;
Reagent 3 = an alkali agent;
Reagent 4 = a reducing agent;
Reagent 5 = an acetone standard solution;
Reagent 6 = a surface active agent; and
Reagent 7 = an anion exchanger.

(B)

Reagent 1 = a radioactive iodide;
Reagent 2 = an oxidizing agent;
Reagent 3 = an alkali agent;
Reagent 4 = a reducing agent;
Reagent 5 = an acetone standard solution; and
Reagent 6' = a non-hydrophilic organic solvent, each of the reagents in the two kits being in separate containers.

18 Claims, 2 Drawing Figures

ULTRAMICRO-QUANTITATIVE DETERMINATION OF ACETONE AND KIT SUITABLE THEREFOR

BACKGROUND OF THE INVENTION

The present invention relates to a process for the ultramicro-quantitative analysis of acetone contained in a sample from a biological preparation and to kits suitable for use in the quantitative analysis.

Acetone is one component of the ketone bodies produced mainly in the liver when mammalians (humans) are subjected to conditions under which the fat stored in the body decomposes, such as a fasting condition. The ketone bodies produced in the liver enter the blood and are transferred mainly to muscles and metabolized therein to supply the energy required for the activity of the muscle cells.

The concentration of the ketone bodies in the blood varies largely depending upon the action of hormones having an influence on the metabolic activity of the organism. The measurement of the concentration of the ketone bodies in the blood has been shown to be of importance in connection with diagnosis, prevention, and treatment of diseases in the field of clinical medicine as well as in basic medical sciences. For example, the concentration of the ketone bodies in the blood has been shown to increase markedly in the case of diabetes and infant periodic emesis. Furthermore, the pancreatic secretion of insulin can be estimated from the degree of reduction in the concentration of the ketone bodies in the blood after a glucose load.

Heretofore, the quantitative determination of the ketone bodies has been carried out by subjecting two components, other than acetone, acetoacetic acid and 3-hydroxybutyric acid, to oxidation and decarboxylation treatments to convert them to acetone and colorimetrically determining the formed acetone. However, this method has not been practical because it has poor detection sensitivity in the quantitative determination of acetone. Instead of this method, a method has been available in the field of basic and clinical medicine in which only either 3-hydroxybutyric acid or acetoacetic acid or both is estimated by an enzymatic method without the determination of acetone.

SUMMARY OF THE INVENTION

The present invention has developed a quite novel radioisotopic process for ultramicro-quantitative determination of acetone. It has been found that it is possible to determine quantitatively a very minute quantity of acetone by advancing a haloform reaction of the acetone contained in a sample from biological preparations with radioactive molecular iodine (or its cationic form) in a strong alkaline solution. Radioactive iodoform thus produced quantitatively can be determined after reducing the nonreacted radioactive molecular or cationic iodine to radioactive iodide which is readily separated from the radioactive iodoform.

The present invention is based on this discovery. By combining the present invention with the method by which 3-hydroxybutyric acid and acetoacetic acid are oxidized to acetone or the method comprising quantitatively determining 3-hydroxybutyric acid and acetoacetic acid by an enzymatic method which has been hitherto used, it is possible to determine quantitatively the ketone bodies contained in the blood and the other tissues in mammalians with a very high sensitivity and simplicity.

According to the present invention in one aspect thereof, briefly summarized, there is provided a process for ultramicro-quantitative analysis of acetone contained in a sample from a biological preparation, which process comprises: reacting radioactive molecular or catioic iodine with acetone contained in the sample in a strong alkaline solution to quantitatively produce radioactive iodoform through a haloform reaction, reducing the nonreacted radioactive molecular or cationic iodine to radioactive iodide to separate the radioactive iodide from the radioactive iodoform, and determining the radioactivity of the radioactive iodoform by a conventional method.

According to this invention in another aspect thereof, briefly summarized, there are provided two types of quantitative assay kits, kit(A) and kit(B), which are used in the practice of the above described process.

(A)

Reagent 1 = a radioactive iodide
Reagent 2 = an oxidizing agent
Reagent 3 = an alkali agent
Reagent 4 = a reducing agent
Reagent 5 = an acetone standard solution
Reagent 6 = a surface active agent
Reagent 7 = an anion exchanger (B)

Reagent 1 = a radioactive iodide
Reagent 2 = an oxidizing agent
Reagent 3 = an alkali agent
Reagent 4 = a reducing agent
Reagent 5 = an acetone standard solution
Reagent 6' = a non-hydrophilic organic solvent The nature, utility, and further features of this invention will be more clearly apparent from the following detailed description beginning with a consideration of general aspects of the invention and concluding with specific examples of practice illustrating preferred embodiment of the invention.

DETAILED DESCRIPTION OF THE INVENTION

The standardized determination method (hereinafter reference to as standardized method) using the kit (A) is as follows.

① 0.5 ml of a sample (or the Reagent 5 (= acetone standard solution)) and 0.1 ml of the Reagent 3 (= sodium hydroxide solution) are mixed in a round-bottomed centrifuge tube of a capacity of about 10 ml, and the centrifuge tube is placed in ice water.

② 0.1 ml of a solution of radioactive iodine having the following composition is prepared under ice cooling; this solution is added to the solution ① and the resultant mixture is immediately mixed thoroughly.

Reagent 2 = iodine chloride solution
(200μ mole/ml) — 0.03 ml
Reagent 1 = radioactive iodide (sodium salt)
(the radioactivity is 10,000 to 100,000 cpm) 0.01 ml ③ The mixed solution ② is kept at a temperature of 0° C. for 30 minutes to complete the formation of iodoform. After this operation, 0.5 ml of a mixture consisting of the Reagent 4 of sodium thiosulfate (0.2 mg/ml), the Reagent 6 of a 20% solution of alkylarylpolyether alcohol, "Triton X-100" (trade name, manufactured by Rohm & Hass Co. U.S.A.)) and distilled water in the ratio of 1:2:2 are added to the resulting solution ②, to reduce the non-reacted radioactive iodine to radioactive iodide and to disperse the radioactive iodoform in the mixture. ④ Thereafter, 100 mg of the Reagent 7 of an anion exchange resin is added to the solution to adsorb the radioactive iodide. Then, 0.5 ml of the supernatant is transferred to a test tube, and the radioactivity of the iodoform contained in the test tube is determined by means of a gamma counter.

Figure 1:
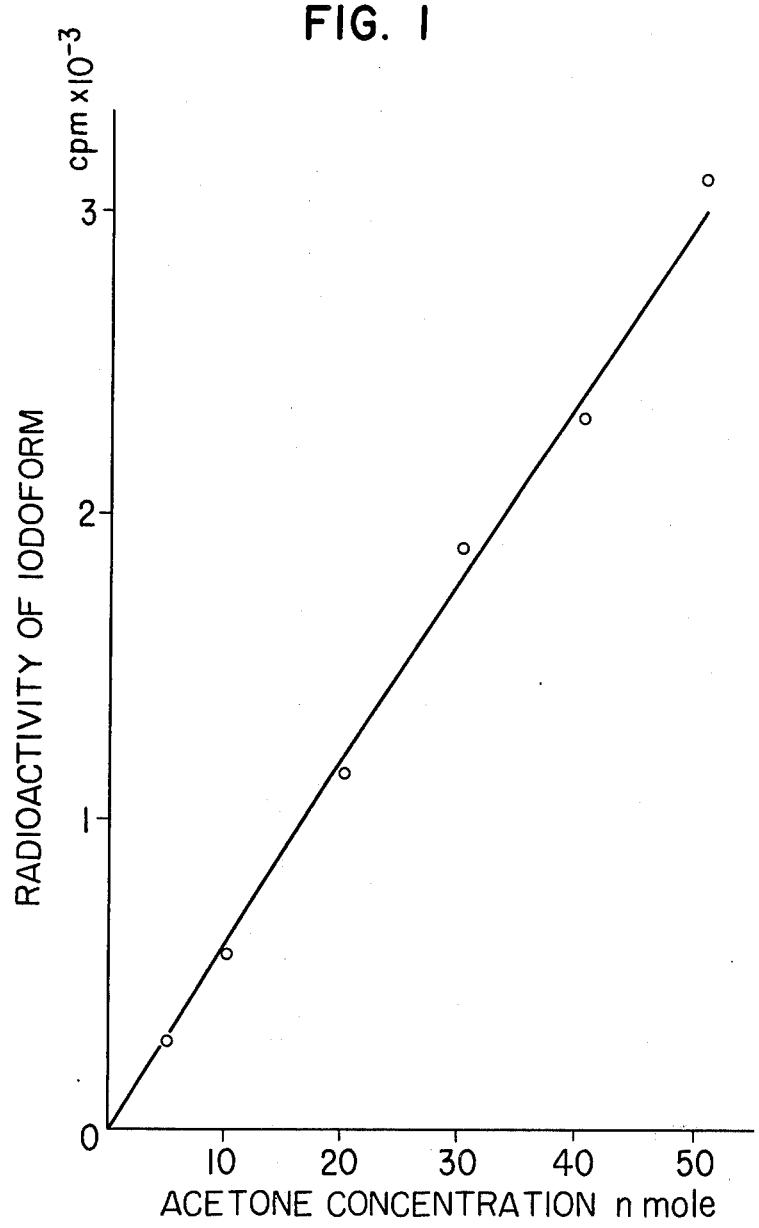
FIG. 1 is a graph showing a standard curve made according to one embodiment of the present invention, wherein the ordinate represents the radioactivity (cpm $\times 10^-$) of iodoform and the abscissa represents the concentration (nmole) of acetone in a sample.

⑤ A standard solution containing 5 to 50 nmoles of acetone (the Reagent 5) is subjected to the above-described procedure to obtain a standard curve as shown in FIG. 1. The quantity of acetone contained in a sample is determined by subjecting the sample to exactly the same standardized determination method and calculating the acetone quantity on the basis of the standard curve.

The validity of the above-described standardized method and the modification of this method with a use of other similar reagents and procedures have been examined, and the results are as follows.

(1) Preparation of a sample

The method for preparing a sample from biological preparations is not particularly limited; any conventional method being utilizable in the preparation of a sample provided that acetone is in a free state in an aqueous solution. For example, in the case of a blood sample, the blood may be used directly as a sample as it is or after a pretreatment such as removal of protein, and if a sample is taken from tissues, the tissues may be subjected to various treatment such as freezing, homogenizing and extracting before prepareing the sample.

In the above-described standardized method using the kit (A), it is sufficient that the quantity of acetone contained in a sample or the standard solution is in the range of 5 to 50 nmole as is shown in the standard curve of FIG. 1. A sample containing larger quantities of acetone may be quantitatively determined by diluting it or increasing the concentration of the reagent 2 and extracting the resulting iodoform with a non-hydrophilic organic solvent (the Reagent 6' of the kit (B)).

(2) Preparation of radioactive molecular or cationic iodine

The formation of iodoform requires molecular iodine or iodine cation. On the other hand, since the radioactive iodo-compund commercially available is sodium iodide, it is necessary to oxidize the iodide. Accordingly, each kit comprises a radioactive iodide as the Reagent 1 and an oxidizing agent as the Reagent 2. In the standardized method, a radioactive iodide and iodine monochloride as an oxidizing agent are mixed to prepare radioactive iodine chloride.

While an iodine chloride solution is stable in a dark bottle kept cold at a concentration of 100μ mole/ml, it becomes unstable when it is diluted and mixed with a radioactive iodide. Therefore, the mixed solution should be used at a temperature of 0° C. within an hour. By using a radioactive iodide without a carrier (non-radioactive iodide), it is possible to prepare iodine chloride of high specific radioactivity. The oxidation of the radioactive iodide may also be carried out by the use of an oxidizing agent other than iodine chloride, such as iodine bromide, molecular iodine, sodium hypochlorite, tosylchloramide sodium (chloramine T), and peroxidase.

(3) Adjustment of a pH of the reaction

The formation of iodoform proceeds a strong alkaline solution. The most suitable concentration of a sodium hydroxide solution (the Reagent 3) in the standardized method has been found to be in the range of 0.4 to 1.0 N. However, since what is necessary is not the sodium hydroxide concentration in such a range, but the pH of the reaction system, the pH may also be adjusted by other alkalisolutions such as aqueous potassium hydroxide and aqueous lithium hydroxide. Each kit of the present invention comprises an alkali agent as the Reagent 3 for the purpose of adjusting the pH of the reaction mixture.

(4) Iodoform formation

Even if the molar ratio of acetone to indine chloride is 1:1, the formation of iodoform proceeds with substantial completeness at a temperature of 0 to 30° C. within 30 minutes. Moles of iodine (I$^+$) which combines with 50 nmoles of acetone is theoretically 150 nmoles. Since the standardized method uses 200 nmoles of iodine chloride, a large quantity of the radioactive iodine added is converted to the iodoform, and it is thus possible to determine a very small quantity of acetone with high sensitivity.

(5) Reduction of non-reacted radioactive iodine

In order to completely reduce the unreacted radioactive molecular or cationic iodine to radioactive iodide any reducing agent, other than sodium thiosulfate, such as sodium hydrogensulfite, is similarly effective. The kits of the present invention comprise, as the reagent 4, a solution or powder of a reducing agent such as those given above.

(6) Separation of non-reacted radioactive iodide from iodoform

Iodoform is very stable and dissolves in non-hydrophilic organic solvents such as benzene, ethyl acetate, chloroform, and ether, while iodides in the aqueous solution do not. Therefore, in order to separate the non-reacted radioactive iodide from indoform, it is possible to extract the iodoform by shaking the reaction mixture with a non-hydrophilic organic solvent in which iodoform is substantially soluble but iodides are substantially insoluble, such as an aromatic hydrocarbon, e.g. benzene, toluene or xylenes, especially benzene; a lower alkyl lower alkaroate, e.g. ethyl acetate or ethyl propionate, especially ethyl acetate; chloroform; and a dilower alkyl ether, e.g. diethyl ether and dipropyl ether, especially diethyl ether. In this case, the quantity of the acetone can be determined by measuring the radioactivity of the organic solvent. The kit (B) of the present invention used for accomplishing this method comprises a non-hydrophilic organic solvent as the Reagent 6'.

However, iodoform resulting from not more than 50 nmoles of acetone, as in the standardized method, is uniformly dispersed and suspended in water in the presence of a surface active agent. Accordingly, if an anion exchanger such as an anion exchange resin is added to the reaction mixture to adsorb all of the non-reacted iodide, it is possible to determine the quantity of the acetone by measuring the radioactivity of the supernatant because all of the radioactivity of the supernatant is due to the suspended iodoform.

The ion exchange adsorption method is advantageous over the organic solvent extraction method in that it is more convenient, entails no risk of the experimenter inhaling the vapor of organic solvents, and requires no installation such as shaker. For a determination method using the ion exchange adsorption method, the kit (A) comprises a surface active agent as the Reagent 6 and an anion exchanger as the Reagent 7.

The type of the surface active agent is not particularly limited. Any surface active agent which functions to disperse uniformly the iodoform in an aqueous solution may be used. Examples of the surface active agent other than alkylarylpolyether alcohol (Triton X-100) which may be used in the standardized method are polyoxyethylene sorbitol fatty acid ester (Tween 20, 60, 80), sodium alkyl sulfate such as sodium lauryl sulfate, and deoxycholic acid.

As the anion exchanger, any conventional anion exchange resin may be always effectively used. Illustrative of such anion exchange resins are strongly basic anion exchange resins such as Dowex-1 and Dowex-2 (manufactured by Dow Chemical, U.S.A.), Amberlite IRA-400, Amberlite IRA-401 and Amberlite IRA-410 (manufactured by Rohm & Hass, U.S.A.), Permutit S-1 and Permutit S-2 (manufactured by the Permutit, U.S.A.) and Bio Rad AG-1 and Bio Rad AG-2 (manufactured by Bio-Rad Laboratories, U.S.A.). These exchangers are used in $Cl^-$—, $HCOD^-$—, $OH^-$— or $HCO_3^-$— form.

As can be seen from the foregoing, the present invention makes it possible to rapidly determine a very minute quantity of acetone contained in a sample from biological preparations on the basis of a new concept of producing radioactive iodoform from acetone.

In order to indicate more fully the nature and utility of this invention, the following specific examples of practice are set forth, it being understood that these examples are presented as illustrative only and that they are not intended to limit the scope of the invention.

EXAMPLE 1

Quantitative determination of the total ketone bodies in the blood of a rat:

Five fasted rats (fasted for 20 hours) and 5 nonfasted rats were decapitated to obtain their blood. To each of the resulting sera were added 3-hydroxybutyric acid dehydrogenase, NAD, lactic dehydrogenase, and pyruvic acid. Resulting mixture was incubated in a tris-(hydroxymethyl) aminomethane buffer solution (PH 8.5) at a temperature of 30° C. for 1 hour to convert the 3-hydroxybutyric acid in the sera to acetoacetic acid by an enzymatic recycling method. After deproteinization with perchloric acid, the reaction mixture was neutralized with potassium hydroxide. Then, a strongly acid cation exchange resin Dowex 50 ($H^+$ form) was added to the neutralized mixture, and the resulting mixture was maintained at a temperature of 50° C. for 2 hours to decarboxylate the acetoacetic acid to acetone. Thereafter, the solution thus treated was treated with an anion exchange resin to remove the pyruvic acid, whereby a supernatant was obtained.

The quantity of acetone in the supernatant as a sample was determined according to the standardized method. The results are shown in the following table.

|  | Quantity of acetone ($\mu$mole/ml blood) |
|---|---|
| Non-fasted group | 0.14 ± 0.06 |
| Fasted group | 1.54 ± 0.24 |

EXAMPLE 2

Quantitative determination of the total ketone bodies in the blood of alloxan diabetic rats.

Three rats rendered diabetes by alloxan were used to determine quantitatively the ketone bodies of the blood according to the procedure described in Example 1. The result was that the quantity of acetone was 2.90 ± 0.26$\mu$ moles/ml plasma.

EXAMPLE 3

Quantitative determination of the quantity of acetone in the cardiac muscle of rats:

The cardiac muscles of 5 fasted rats and 5 nonfasted rats were homogenized separately. After deproteinization with perchloric acid, the resulting mixtures were neutralized with potassium hydroxide. The supernatant thus obtained was subjected to the standardized method to determine quantitatively the acetone contained therein. The results are shown in the following table.

|  | Quantity of acetone ($\mu$ mole/g tissue) |
|---|---|
| Non-fasted group | 42.8 ± 7.8 |
| Fasted group | 21.4 ± 2.5 |

EXAMPLE 4

Periodical changes in the total ketone bodies concentration in blood after insulin administration:

According to the procedure described in Example 1, blood samples were prepared from three rats 0, 30, 60, 90 and 120 minutes after subcutaneous injection of insulin.

Each sample was subjected to the standardized method through the processes ① and ② and was left to stand at a temperature of 0° C. for 30 minutes to advance the iodoform reaction. Thereafter, 0.1 ml of sodium thiosulfate (0.2 mg/ml) (the Reagent 4) and 0.2 ml of distilled water were added to the reaction mixture to reduce the non-reacted radioactive iodine to radioactive iodine anion. 1.5 ml of benzene (the Reagent 6' of the kit (B)) was then added to the solution so treated, which was then amply shaken, whereby the radioactive iodoform was extracted into a benzene layer. 1 ml of the supernatant of the benzene layer was subjected to radioactivity measurement. The acetone standard solution was subjected to the same operation to determine quantitatively the acetone contained in the sample from the standard curve made.

Figure 2:
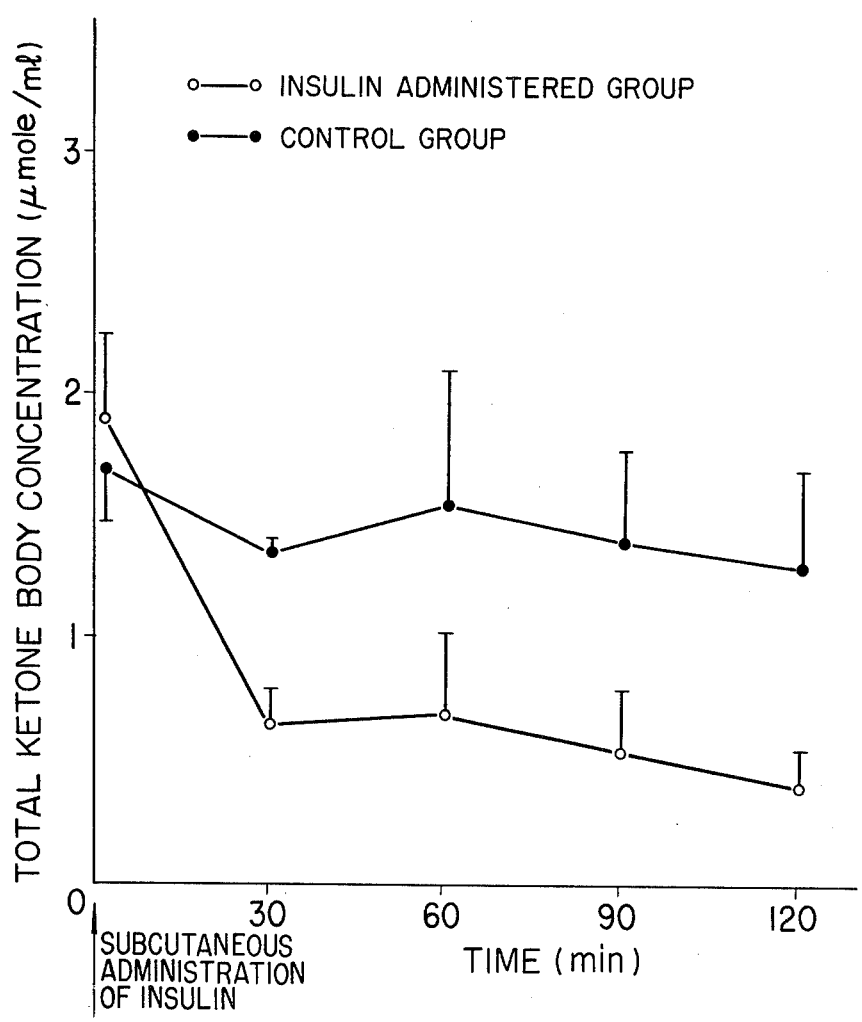
FIG. 2 is a graph showing a periodical change in the blood concentration of total ketone bodies when insulin is administered to a rat (Example 4), as determined by the present invention; the ordinate represents the quantity ($\mu$mole) of the total ketone bodies in terms of acetone and the abscissa represents the elapsed time (minutes) after the administration of insulin.

The results are shown in FIG. 2 together with the results relating to a control group to which no insulin was administered.

We claim:

1. A process for the ultramicro-quantitative determination of acetone which comprises reacting radioactive molecular or cationic iodine with the acetone contained in a sample from a biological preparation in a strong alkaline solution to quantitatively produce radioactive iodoform according to a haloform reaction, reducing the non-reacted radioactive molecular or cationic iodine to radioactive iodide separating the radioactive iodide from the radioactive iodoform, and measuring the radioactivity of the radioactive iodoform.

2. A process as claimed in claim 1, wherein the radioactive molecular or cationic iodine is obtained by interaction of the radioactive iodine anion with an oxidizing agent.

3. A process as claimed in claim 2, wherein the oxidizing agent is selected from the group consisting of iodine chloride, iodine bromide, molecular iodine, sodium hypochlorite, tosylchloramide sodium, and peroxidase.

4. A process as claimed in claim 1, wherein the non-reacted radioactive molecular or cationic iodine is reduced to radioactive iodide ion by interaction thereof with a reducing agent selected from the group consisting of sodium thiosulfate and sodium hydrogensulfite.

5. A process as claimed in claim 1, wherein the radioactive iodide ion is separated by contacting an anion exchanger with the aqueous solution containing the radioactive iodoform and the radioactive iodide thereby to adsorb the radioactive iodide.

6. A process as claimed in claim 5, wherein a surface active agent is introduced into the supernatant containing the radioactive iodoform to disperse uniformly the radioactive iodoform therein, and the supernatant is then subjected to a radioactivity measurement.

7. A process as claimed in claim 1, wherein the radioactive iodide ion is separated by shaking the aqueous solution containing the radioactive iodoform and the radioactive iodide with a non-hydrophilic organic solvent in which iodoform is substantially soluble but the iodide is substantially insoluble to dissolve the radioactive iodoform into the solvent.

8. An assay kit for use in ultramicroquantitative analysis of acetone comprising containers of the following reagents, wherein each reagent is in a separate container:

Reagent 1 = a radioactive iodide;
Reagent 2 = an oxidizing agent;
Reagent 3 = an alkali agent;
Reagent 4 = a reducing agent;
Reagent 5 = an acetone standard solution;
Reagent 6 = a surface active agent; and
Reagent 7 = an anion exchanger.

9. An assay kit as claimed in claim 8, wherein the oxidizing agent of the Reagent 2 is selected from the group consisting of iodine chloride, iodine bromide, molecular iodine, sodium hypochlorite, tosylchloramide sodium, and peroxidase.

10. An assay kit as claimed in claim 8 wherein the alkali agent of the Reagent 3 is selected from the group consisting of sodium hydroxide, potassium hydroxide and lithium hydroxide.

11. An assay kit as claimed in claim 8, wherein the reducing agent of the Reagent 4 is selected from the group consisting of sodium thiosulfate and sodium hydrogensulfite.

12. An assay kit as claimed in claim 8, wherein the surface active agent of the Reagent 6 is selected from the group consisting of alkylarylpolyether alcohol, polyoxyethylene sorbitol fatty acid ester, sodium alkyl sulfate and deoxycholic acid.

13. An assay kit for use in the ultramicro-quantitative analysis of acetone comprising containers of the following reagents wherein each reagent is in a separate container comprising:

Reagent 1 = a radioactive iodide;
Reagent 2 = an oxidizing agent;
Reagent 3 = an alkali agent;
Reagent 4 = a reducing atent;
Reagent 5 = an acetone standard solution; and
Reagent 6' = a nonhydrophilic organic solvent.

14. An assay kit as claimed in claim 13, wherein the oxidizing agent of the Reagent 2 is selected from the group consisting of iodine chloride, iodine bromide, molecular iodine, sodium hypochlorite, tosylchloramide sodium, and peroxidase.

15. An assay kit as claimed in claim 14, wherein the alkali agent of the Reagent 3 is selected from the group consisting of sodium hydroxide, potassium hydroxide, and lithium hydroxide.

16. An assay kit as claimed in claim 13, wherein the reducing agent of the Reagent 4 is selected from the group consisting of sodium thiosulfate and sodium hydrogensulfite.

17. An assay kit as claimed in claim 13, wherein the non-hydrophilic organic solvent is a solvent in which iodoform is substantially soluble but the iodide is substantially insoluble, which is selected from the group consisting of aromatic hydrocarbons, lower alkyl lower alkanoates, chloroform, and diloweralkylethers.

18. An assay kit as claimed in claim 13, wherein the non-hydrophilic organic solvent of the reagent 6' is selected from the group consisting of benzene, ethyl acetate, chloroform, and ether.

* * * * *